US00PP37316P3

(12) United States Plant Patent
Gomes da Costa

(10) Patent No.: US PP37,316 P3
(45) Date of Patent: Mar. 10, 2026

(54) ***MANDEVILLA* PLANT NAMED 'TVMD1232'**

(50) Latin Name: *Mandevilla sanderi*
Varietal Denomination: TVMD1232

(71) Applicant: NICOLAAS JOSEF SCHOENMAKER e OUTROS, Sao Paulo (BR)

(72) Inventor: Everton Gomes da Costa, Sao Paulo (BR)

(73) Assignee: NICOLAAS JOSEF SCHOENMAKER e OUTROS, Sao Paulo (BR)

( * ) Notice: Subject to any disclaimer, the term of this patent is extended or adjusted under 35 U.S.C. 154(b) by 0 days.

(21) Appl. No.: 19/313,647

(22) Filed: Aug. 28, 2025

(65) Prior Publication Data

US 2026/0068790 P1 Mar. 5, 2026

Related U.S. Application Data

(60) Provisional application No. 63/689,809, filed on Sep. 2, 2024.

(51) Int. Cl.
*A01H 5/02* (2018.01)

(52) U.S. Cl.
USPC ..... Plt./232

(58) Field of Classification Search
USPC ..... Plt./232
CPC . A01H 5/02; A01H 5/00; A01H 6/088; A01H 6/08
See application file for complete search history.

(56) References Cited

U.S. PATENT DOCUMENTS

PP28,277 P3 * 8/2017 Misato ..... Plt./232

* cited by examiner

*Primary Examiner* — June Hwu
(74) *Attorney, Agent, or Firm* — C. Anne Whealy

(57) ABSTRACT

A new and distinct cultivar of *Mandevilla* plant named 'TVMD1232', characterized by its upright to outwardly spreading plant habit; moderately vigorous to vigorous growth habit; early and freely flowering habit; orangish yellow-colored flowers with orangish yellow-colored throats; and good container and garden performance.

1 Drawing Sheet

Botanical designation: *Mandevilla sanderi.*
Cultivar denomination: 'TVMD1232'.

BACKGROUND OF THE INVENTION

The present invention relates to a new and distinct cultivar of *Mandevilla* plant, botanically known as *Mandevilla sanderi*, and hereinafter referred to by the name 'TVMD1232'.

The new *Mandevilla* plant is a product of a planned breeding program conducted by the Inventor in Sao Paulo, Brazil. The objective of the breeding program is to develop new compact and freely flowering *Mandevilla* plants with large flowers and good garden performance.

The new *Mandevilla* plant originated from a cross-pollination in September 2019 in Sao Paulo, Brazil of *Mandevilla sanderi* 'TVMD654', disclosed in U.S. Plant Pat. No. 35,732, as the female, or seed, parent with a proprietary selection of *Mandevilla sanderi* identified as code number TVMD874, not patented, as the male, or pollen, parent. The new *Mandevilla* plant was discovered and selected by the Inventor as a single flowering plant from within the progeny of the stated cross-pollination grown in a controlled greenhouse environment in Sao Paulo, Brazil in July 2021.

Asexual reproduction of the new *Mandevilla* plant by terminal stem cuttings in a controlled environment in Sao Paulo, Brazil since December 2021 has shown that the unique features of this new *Mandevilla* plant are stable and reproduced true to type in successive generations.

SUMMARY OF THE INVENTION

Plants of the new *Mandevilla* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'TVMD1232'. These characteristics in combination distinguish 'TVMD1232' as a new and distinct *Mandevilla* plant:

1. Upright to outwardly spreading plant habit.
2. Moderately vigorous to vigorous growth habit.
3. Early and freely flowering habit.
4. Orangish yellow-colored flowers with orangish yellow-colored throats.
5. Good container and garden performance.

Plants of the new *Mandevilla* can be compared to plants of the female parent, 'TVMD654'. Plants of the new *Mandevilla* differ primarily from plants of 'TVMD654' in the following characteristics:

1. Flowers of plants of the new *Mandevilla* are larger than flowers of plants of 'TVMD654'.
2. Flowers of plants of the new *Mandevilla* are orangish yellow in color with orangish yellow-colored throats whereas flowers of plants of 'TVMD654' are bright yellow in color with yellow-colored throats.

Plants of the new *Mandevilla* can be compared to plants of the male parent selection. Plants of the new *Mandevilla* differ primarily from plants of the male parent selection in the following characteristics:

1. Flowers of plants of the new *Mandevilla* are smaller than flowers of plants of the male parent selection.
2. Flowers of plants of the new *Mandevilla* are orangish yellow in color whereas flowers of plants of the male parent selection are bright yellow in color.

Plants of the new *Mandevilla* can also be compared to plants of *Mandevilla hybrida* 'Sunpapri', disclosed in U.S. Plant Pat. No. 28,277. In side-by-side comparisons, plants of the new *Mandevilla* differ primarily from plants 'Sunpapri' in the following characteristics:

1. Plants of the new *Mandevilla* have smaller flowers than plants of 'Sunpapri'.
2. Plants of the new *Mandevilla* have orangish yellow-colored flowers whereas plants of 'Sunpapri' have light to pale orange-colored flowers.

BRIEF DESCRIPTION OF THE PHOTOGRAPH

The accompanying colored photograph illustrates the overall appearance of the new *Mandevilla* plant showing the colors as true as it is reasonably possible to obtain in colored reproductions of this type. Colors in the photograph may differ slightly from the color values cited in the detailed botanical description which accurately describe the actual colors of the new *Mandevilla* plant.

The photograph is a side perspective view of a typical flowering plant of 'TVMD1232' grown in a container.

DETAILED BOTANICAL DESCRIPTION

The aforementioned photograph and following observations, measurements and values describe plants grown in July in 15-cm containers in a polyethylene-covered greenhouse in Sao Paulo, Brazil and under cultural practices typical of commercial *Mandevilla* production. During the production of the plants, day temperatures ranged from 20° C. to 35° C. and night temperatures ranged from 10° C. to 20° C. Plants were pinched three times: four weeks, six weeks and eight weeks after planting. Plants were 33 weeks old when the photograph and description were taken. In the following description, color references are made to The Royal Horticultural Society Colour Chart, 2015 Edition, except where general terms of ordinary dictionary significance are used.

Botanical classification: *Mandevilla sanderi* 'TVMD1232'.

Parentage:

*Female, or seed, parent.*—*Mandevilla sanderi* 'TVMD654', disclosed in U.S. Plant Pat. No. 35,732.

*Male, or pollen, parent.*—Proprietary selection of *Mandevilla sanderi* identified as code number TVMD874, not patented.

Propagation:

*Type.*—By vegetative cuttings.

*Time to initiate roots, summer.*—About three weeks at temperatures about 20° C. to 35° C.

*Time to initiate roots, winter.*—About three weeks at temperatures about 20° C. to 25° C.

*Time to produce a rooted young plant, summer.*—About 20 to 25 days at temperatures about 20° C. to 35° C.

*Time to produce a rooted young plant, winter.*—About 25 to 30 days at temperature about 20° C. to 25° C.

*Root description.*—Thick, fleshy; typically white in color, actual color of the roots is dependent on substrate composition, water quality, fertilizers, substrate temperature and physiological age of roots.

*Rooting habit.*—Low branching; medium density.

Plant description:

*Plant and growth habit.*—Upright to outwardly plant habit; roughly broadly obovate in overall shape; moderately vigorous to vigorous growth habit and moderate to rapid growth rate.

*Plant height, soil level to top of foliar plane.*—About 25 cm.

*Plant height, soil level to top of floral plane.*—About 35 cm.

*Plant diameter (spread).*—About 18 cm.

*Lateral branch description.*—Branching habit: Moderate branching habit, typically about two primary lateral branches each with about two secondary lateral branches. Length: About 15 cm. Diameter: About 3 mm. Internode length: About 3 cm. Aspect Primary lateral branches, mostly upright; secondary lateral branches, about 30° from primary branch axis. Strength: Moderately strong. Texture and luster: Smooth, glabrous; semi-glossy; becoming woody with development. Color, developing: Close to 143C. Color, developed: Close to 144B, when woody, close to 199B.

Leaf description:

*Arrangement.*—Opposite, simple.

*Length.*—About 5.5 cm.

*Width.*—About 3 cm.

*Shape.*—Obovate to ovate.

*Apex.*—Abruptly acuminate.

*Base.*—Rounded cordate.

*Margin.*—Entire; not lobed.

*Texture and luster, upper and lower surfaces.*—Smooth, glabrous; moderately coriaceous; semi-glossy.

*Venation pattern.*—Pinnate.

*Color.*—Developing leaves, upper surface: Close to 144A. Developing leaves, lower surface: Close to 143D. Fully expanded leaves, upper surface: Close to 139A; venation, close to 143B. Fully expanded leaves, lower surface: Close to 138B; venation, close to 143B.

*Petioles.*—Length: About 1 cm. Diameter: About 2 mm. Strength: Moderately strong. Texture and luster, upper and lower surfaces: Smooth, glabrous; slightly glossy. Color, upper and lower surfaces: Close to 143B.

Flower description:

*Flower type and flowering habit.*—Single salverform flowers arranged in terminal and axillary cymes; flowers face mostly upright to outwardly; freely flowering habit with about four fully open flowers per inflorescence and about 45 flower buds and open flowers developing per plant.

*Natural flowering season.*—Plants flower continuously year-round in Brazil; plants begin flowering about 25 weeks after planting rooted young plants.

*Flower longevity on the plant.*—Individual flowers last about ten days; flowers not persistent.

*Fragrance.*—None detected.

*Inflorescence height*.—About 14 cm.

*Inflorescence diameter*.—About 11 cm.

*Flower buds*.—Length: About 4 cm. Diameter: About 6.3 mm. Shape: Lanceolate. Texture and luster: Smooth, glabrous; slightly glossy. Color: Close to 16C and towards the apex, close to 14B.

*Flowers*.—Appearance: Flared trumpet, corolla fused and five-parted. Diameter: About 5.8 cm by 5.8 cm. Depth (length): About 3 cm. Throat diameter: About 7 mm. Tube length: About 1 cm. Tube diameter: About 3 mm.

Corolla.—Quantity and arrangement: Five petals arranged in a single whorl; lower 50% portion of the petals are fused into a funnelform tube. Petal length: About 2.5 cm. Petal width: About 1.3 cm. Petal shape and appearance: Unequal and asymmetric; roughly spatulate; slightly convex. Petal apex: Acute. Petal margin: Entire; slightly undulate. Petal texture and luster, upper and lower surfaces: Smooth, glabrous; slightly glossy. Throat texture: Smooth, glabrous. Tube texture: Smooth, glabrous. Color: Petal, when opening and fully opened, upper surface: Close to 21B; venation, close to 32C; color does not change with subsequent development. Petal, when opening and fully opened, lower surface: Close to 18A; venation, close to 18A; color does not change with subsequent development. Throat: Close to 21B; venation, close to 32C. Tube: Close to 151B; venation, close to 151B.

*Sepals*.—Quantity and arrangement: Five sepals arranged in a single whorl. Length: About 4 mm. Width: About 3 mm. Shape: Lanceolate. Apex: Narrowly acuminate. Base: Broadly cuneate and fused. Margin: Entire. Texture and luster, upper surface: Smooth, glabrous; slightly glossy. Texture and luster, lower surface: Smooth, glabrous; matte. Color: When developing, upper and lower surfaces: Close to 145B. Fully developed, upper and lower surfaces: Close to 145B.

*Peduncles*.—Length: About 5 cm. Diameter: About 1.8 mm. Strength: Strong. Aspect: About 85° from lateral branch axis. Texture and luster: Smooth, glabrous; moderately glossy. Color: Close to 144A.

*Pedicels*.—Length: About 1.8 cm. Diameter: About 1.3 mm. Strength: Moderately strong. Aspect: About 85° from peduncle axis. Texture and luster: Smooth, glabrous; moderately glossy. Color: Close to 144B.

*Reproductive organs*.—Stamens: Quantity and arrangement: Typically five; basifixed; anthers connivent. Filament length: About 2 mm. Filament color: Close to 145B. Anther shape: Narrowly sagittate. Anther size: About 3 mm by 10 mm. Anther color: Close to 160B. Pollen amount: Moderate. Pollen color: Close to 155B. Pistils: Quantity: Typically one. Pistil length: About 2.6 cm. Style length: About 2 cm. Style color: Close to 145D. Stigma diameter: About 1.6 mm. Stigma shape: Club-shaped, pointed. Stigma color: Close to 145D. Ovary color: Close to 145B.

*Seeds and fruits*.—To date, seed and fruit production have not been observed on plants of the new *Mandevilla*.

Pathogen & pest resistance: To date, plants of the new *Mandevilla* have not been noted to be resistant to pathogens and pests common to *Mandevilla* plants.

Temperature tolerance: Plants of the new *Mandevilla* have been observed to tolerate temperatures ranging from about 5° C. to about 40° C. and to be suitable for USDA Hardiness Zones 9 to 13.

It is claimed:

1. A new and distinct *Mandevilla* plant named 'TVMD1232' as herein illustrated and described.

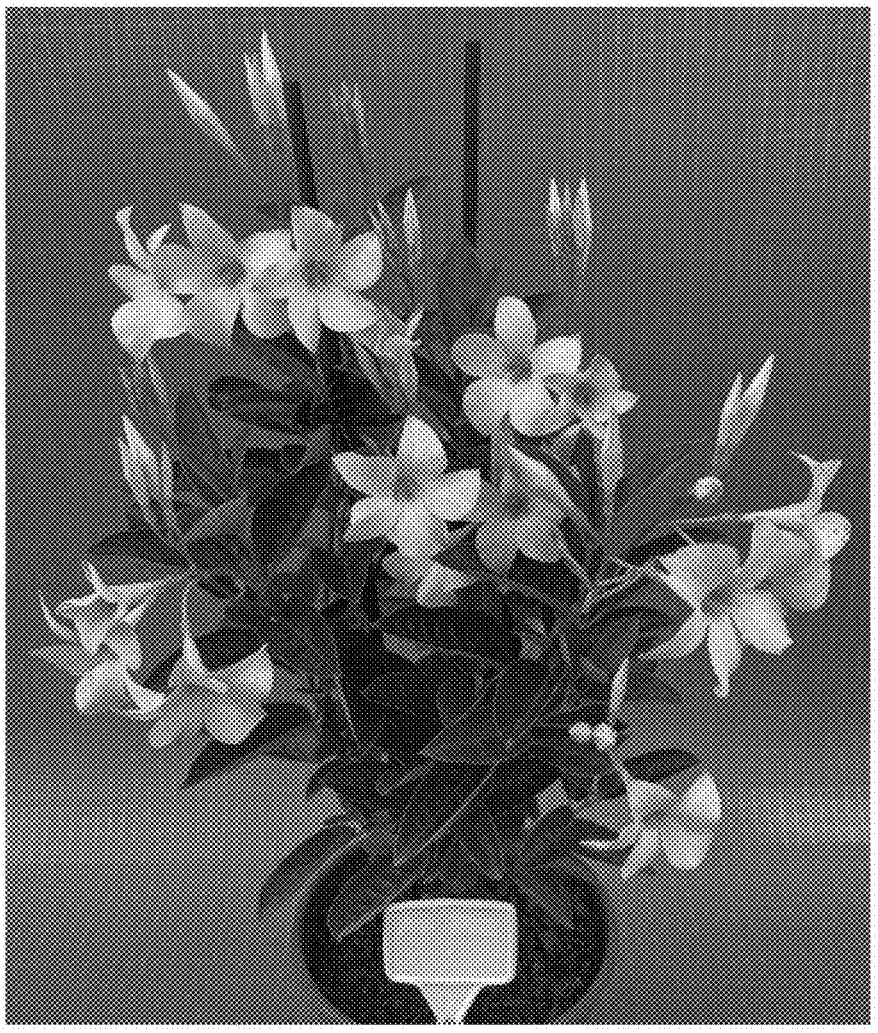

* * * * *